United States Patent
Natsuyama et al.

(10) Patent No.: US 12,023,647 B2
(45) Date of Patent: Jul. 2, 2024

(54) METHOD FOR REUSING ZEOLITE ADSORBENT AND REGENERATED ADSORBENT

(71) Applicant: SEKISUI CHEMICAL CO., LTD., Osaka (JP)

(72) Inventors: Kazuto Natsuyama, Tsukuba (JP); Kokoro Hamachi, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 591 days.

(21) Appl. No.: 17/275,429

(22) PCT Filed: Sep. 25, 2019

(86) PCT No.: PCT/JP2019/037632
§ 371 (c)(1),
(2) Date: Mar. 11, 2021

(87) PCT Pub. No.: WO2020/067177
PCT Pub. Date: Apr. 2, 2020

(65) Prior Publication Data
US 2022/0040673 A1 Feb. 10, 2022

(30) Foreign Application Priority Data
Sep. 25, 2018 (JP) ................. 2018-179528

(51) Int. Cl.
*B01J 20/34* (2006.01)
*B01D 53/047* (2006.01)
(Continued)

(52) U.S. Cl.
CPC ........ *B01J 20/3408* (2013.01); *B01D 53/047* (2013.01); *B01J 20/18* (2013.01);
(Continued)

(58) Field of Classification Search
CPC .... B01J 20/3408; B01J 20/18; B01J 20/3483; B01D 53/047; C01B 32/50; C01B 3/56;
(Continued)

(56) References Cited

U.S. PATENT DOCUMENTS 4,433,981 A * 2/1984 Slaugh ................. B01J 20/041
95/139
8,916,490 B2 * 12/2014 Chewter ................ C07C 11/06
502/34
(Continued)

FOREIGN PATENT DOCUMENTS

| CA | 2298125 A1 * | 9/2000 | ......... B01D 53/0462 |
| CN | 1131053 A | 9/1996 | |

(Continued)

OTHER PUBLICATIONS

Office Action dated Nov. 30, 2022 from the China National Intellectual Property Administration in CN Application No. 201980058225.3.

(Continued)

*Primary Examiner* — Patricia L. Hailey
(74) *Attorney, Agent, or Firm* — Sughrue Mion, PLLC (57) ABSTRACT

Provided is a method for reusing an adsorbent which can stably exhibit purification ability by regenerating a used absorbent, in order to keep the composition of a purified syngas constant.
The present invention concerns a method for regenerating a zeolite adsorbent which adsorbs a carbon dioxide gas from a syngas comprising the carbon dioxide gas and reduces the concentration of the carbon dioxide gas in the syngas, comprising: a step of recovering a used zeolite adsorbent; a step of calcining the used zeolite adsorbent at a temperature of 300° C. to 600° C. in an oxygen atmosphere to produce
(Continued)

a regenerated zeolite adsorbent; and a step of reusing the regenerated zeolite adsorbent.

6 Claims, 1 Drawing Sheet

(51) Int. Cl.
  *B01J 20/18* (2006.01)
  *C01B 3/56* (2006.01)
  *C01B 32/50* (2017.01)

(52) U.S. Cl.
  CPC ............... *C01B 3/56* (2013.01); *C01B 32/50* (2017.08); *C01B 2203/0405* (2013.01); *C01B 2203/046* (2013.01); *C01B 2203/0475* (2013.01); *C01B 2203/0485* (2013.01); *C01B 2203/147* (2013.01)

(58) Field of Classification Search
  CPC ...... C01B 2203/0405; C01B 2203/046; C01B 2203/0475; C01B 2203/0485; C01B 2203/147
  USPC .................. 502/38, 53, 50, 56, 60; 423/700
  See application file for complete search history.

(56) References Cited

U.S. PATENT DOCUMENTS

| | | | | |
|---|---|---|---|---|
| 2003/0181738 A1* | 9/2003 | Muller | ..................... | B01J 38/10 502/53 |
| 2003/0187286 A1* | 10/2003 | Teles | ........................ | B01J 29/90 549/531 |
| 2004/0200758 A1 | 10/2004 | Yang et al. | | |
| 2006/0117952 A1 | 6/2006 | Bancon et al. | | |
| 2008/0156190 A1 | 7/2008 | Lutz et al. | | |
| 2014/0357919 A1* | 12/2014 | Sadasivan Vijayakumari | ............. | B01J 38/12 585/653 |
| 2017/0260552 A1 | 9/2017 | Haas et al. | | |

FOREIGN PATENT DOCUMENTS

| | | | | |
|---|---|---|---|---|
| CN | 1378480 A | | 11/2002 | |
| CN | 1420078 A | | 5/2003 | |
| CN | 1917952 A | | 2/2007 | |
| EP | 3 476 920 A1 | | 5/2019 | |
| GB | 1 551 348 A | | 8/1979 | |
| JP | 52-038498 A | | 3/1977 | |
| JP | 2-111621 A | | 4/1990 | |
| JP | 6-254395 A | | 9/1994 | |
| JP | H06-254395 A | * | 9/1994 | ............. B01D 53/04 |
| JP | 8-252419 A | | 10/1996 | |
| JP | 2002-177773 A | | 6/2002 | |
| JP | 2003-511218 A | | 3/2003 | |
| JP | 2003-246606 A | | 9/2003 | |
| JP | 2010221188 A | * | 10/2010 | ............. B01J 20/34 |
| JP | 2011-001264 A | | 1/2011 | |
| WO | 2017/221987 A1 | | 12/2017 | |
| WO | WO-2020158752 A1 | * | 8/2020 | ................ C12P 7/06 |

OTHER PUBLICATIONS

Communication, dated Apr. 8, 2021, issued by The International Bureau of WIPO in counterpart application No. PCT/JP2019/037632.
Extended European Search Report, dated Jun. 1, 2022, in European Application No. 19864029.4.
Notice of Reasons for Refusal, dated Feb. 14, 2020, issued by the Japanese Patent Office in Japanese Patent Application No. 2019-555047.
International Search Report for PCT/JP2019/037632, dated Dec. 24, 2019 (PCT/ISA/210).

\* cited by examiner

METHOD FOR REUSING ZEOLITE ADSORBENT AND REGENERATED ADSORBENT

CROSS REFERENCE TO RELATED APPLICATIONS

This application is a National Stage of International Application No. PCT/JP2019/037632, filed Sep. 25, 2019, claiming priority based on Japanese Patent Application No. 2018-179528, filed Sep. 25, 2018.

BACKGROUND OF THE INVENTION

Field of the Invention

The present invention relates to a method for reusing a zeolite adsorbent, and more particularly to a method for reusing a zeolite adsorbent used in a pressure swing adsorption apparatus for reducing the concentration of carbon dioxide gas in a syngas. The present invention also relates to a regenerated adsorbent comprising a calcined product of a used zeolite adsorbent.

Background Art

In recent years, methods for producing various organic substances from materials other than petroleum have been studied in view of concerns about depletion of fossil fuel resources due to mass consumption of oils and alcohols produced from petroleum as a raw material and global environmental problems such as increase of carbon dioxide in the atmosphere. For example, a method for producing bioethanol from an edible raw material such as corn by a sugar fermentation method has been of interest. However, the sugar fermentation method using such edible raw materials has a problem of bringing about price escalation of food, for example, since the limited farmland area will be used for the production of products other than food.

In order to solve such a problem, studies have been carried out on various methods for producing various organic substances which have been conventionally produced from petroleum, using non-edible raw materials which have been conventionally disposed. For example, syngas containing carbon dioxide, carbon monoxide, and hydrogen has been converted to acetic acid and ethanol by microbial fermentation. When contaminants or impurities are present in the syngas or the raw material gas in such a method for producing ethanol from a syngas by microbial fermentation, there was a problem that an organic substance cannot be efficiently obtained since the microbial fermentation is inhibited. In order to solve such a problem, syngases have been obtained by purifying raw material gases.

However, even when use was made to a syngas from which contaminants and impurities have been removed by purification, there still remained a problem that an organic substance cannot be efficiently obtained depending on the gas composition in the syngas. Therefore, Patent Document 1 proposes a method for purifying a syngas containing hydrogen and carbon monoxide and/or nitrogen as the main components and contaminated with carbon dioxide and, optionally, one or more other impurities, in which the carbon dioxide in the syngas is removed by a pressure swing adsorption method using zeolite as an adsorbent.

PRIOR ART DOCUMENTS

Patent Literature

Patent Document 1: JP2003-246606 A

SUMMARY OF THE INVENTION

Problem to be Solved by the Invention

When the present inventors have conducted purification of a syngas over a long period of time using zeolite as in the method described in Patent Document 1, the performance of the adsorbent zeolite decreased, which stopped providing a sufficient effect of purification. To such issue, although the adsorbent zeolite was replaced with a new (unused) zeolite, a new problem was found that the purification ability was unstable for a certain period from the start of use, and the gas composition in the syngas was not kept constant.

Therefore, the object of the present invention is to provide a method for reusing an adsorbent capable of stably exhibiting purification ability by regenerating a used adsorbent in order to maintain a constant composition of a purified syngas.

Means for Solving the Problem

The present inventors have found that the purification ability can be stably exhibited and the above problem can be solved by regenerating a used zeolite adsorbent into a specific state and subsequently using the regenerated zeolite adsorbent, without replacing the used zeolite adsorbent with a new (unused) zeolite adsorbent. That is, the summary of the present invention is as follows.

[1] A method for regenerating a zeolite adsorbent which adsorbs a carbon dioxide gas from a syngas comprising the carbon dioxide gas and reduces the concentration of the carbon dioxide gas in the syngas, comprising:
 a step of recovering a used zeolite adsorbent;
 a step of calcining the used zeolite adsorbent at a temperature of 300° C. to 600° C. in an oxygen atmosphere to produce a regenerated zeolite adsorbent; and
 a step of reusing the regenerated zeolite adsorbent.
[2] The method according to [1], wherein the zeolite adsorbent is used in a pressure swing adsorption apparatus.
[3] The method according to [1] or [2], wherein the amount of carbon compound attached to the regenerated zeolite adsorbent is 1.0 mass % or less in terms of carbon atoms with respect to the zeolite adsorbent, and the amount of sulfur compound attached to the regenerated zeolite adsorbent is 0.01 mass % to 0.8 mass % in terms of sulfur atoms with respect to the zeolite adsorbent.
[4] The method according to any one of [1] to [3], wherein the syngas comprises a tar component.
[5] The method according to any one of [1] to [4], wherein the zeolite adsorbent comprises an LSX type zeolite.
[6] The method according to any one of [1] to [5], wherein the syngas comprises carbon monoxide, hydrogen, and nitrogen.
[7] The method according to any one of [1] to [6], wherein the syngas is derived from MSW.
[8] A regenerated zeolite adsorbent obtained by regenerating a used zeolite adsorbent, wherein
 a carbon compound and a sulfur compound are attached to the regenerated zeolite adsorbent, and wherein
 the attached amount of the carbon compound is 1.0 mass % or less in terms of carbon atoms, with respect to the zeolite adsorbent, and the attached amount of the sulfur compound is 0.01 to 0.8 mass % in terms of sulfur atoms, with respect to the zeolite adsorbent.

[9] The regenerated adsorbent according to [8], wherein the zeolite adsorbent comprises an LSX type zeolite.

Effect of the Invention

According to the present invention, it is possible to provide a method for reusing an adsorbent capable of stably exhibiting purification ability in order to maintain a constant composition of a purified syngas. The syngas can be purified stably by using the regenerated adsorbent obtained by the method of the present invention.

EMBODIMENT OF THE INVENTION

Hereinafter, one example of a preferred embodiment to carry out the present invention will be described. However, the following embodiments are examples for explaining the present invention, and the present invention shall not be limited to the following embodiments. Unless otherwise specified in the present specification, the presence ratio of each component in the gas is a ratio that is volume based instead of mass based. Thus, unless otherwise specified, percent % represents volume % and ppm represents volume ppm.

<Method of Reusing Zeolite Adsorbent>

Figure 1:
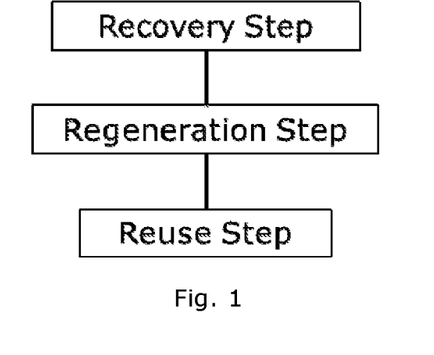
FIG. 1 is a process flow diagram showing one example of a method for reusing a zeolite adsorbent according to the present invention.

The present invention is a method for reusing a zeolite adsorbent, comprising a recovery step, a regeneration step, and a reuse step (see FIG. 1). Hereinafter, each step in the reuse method according to the present invention will be described in details.

(Recovery Step)

A recovery step is a step of recovering the used zeolite adsorbent (see FIG. 1). In the present specification, "used" means a case where the zeolite has 80% or less of carbon dioxide adsorption ability with respect to the carbon dioxide adsorption ability of a new (unused) zeolite adsorbent.

The used zeolite adsorbent is not particularly limited as long as it can adsorb a carbon dioxide gas contained in the syngas. More specifically, the zeolite adsorbent may further comprise a binder or the like in addition to the zeolite. The used zeolite may also contain a carbon compound and a sulfur compound.

Examples of the zeolite include, without particular limitation, LTA type zeolite, FER type zeolite, MWW type zeolite, MFI type zeolite, MOR type zeolite, LTL type zeolite, FAU type zeolite, and BEA type zeolite. Among these, preferred is FAU type zeolite, more preferred are X type zeolite, Y type zeolite, and LSX type zeolite, and further preferred is LSX type zeolite.

The zeolite contains a silicon atom (Si), an aluminum atom (Al), and an oxygen atom (O). In this case, the Si/Al (molar) ratio is preferably 0.5 to 5.0, more preferably 0.7 to 3.0, further preferably 0.9 to 2.0, and particularly preferably 1.1 to 1.5.

The zeolite may further contain at least one of gallium (Ga), germanium (Ge), boron (B), zinc (Zn), phosphorus (P), zirconium (Zr), titanium (Ti), chromium (Cr), beryllium (Be), vanadium (V), arsenic (As), and the like, as needed.

Further, a cation contained in the zeolite preferably contains lithium, sodium, or proton, and more preferably contains lithium.

The above-mentioned zeolites may be used alone or two or more of those in combination.

The content of zeolite in the zeolite adsorbent is preferably 50 mass % or more, more preferably 75 mass % or more, and further preferably 95 mass % or more with respect to the zeolite adsorbent.

Examples of the binder include, without particular limitation, alumina, silica, silica-alumina, titania-alumina, zirconia-alumina, boria-alumina, clay (kaolin, attapulgite, bentonite), metal oxides, and the like. Among these, preferred are alumina, silica-alumina, and boria-alumina, in view of having a strong binding force to the zeolite and a high specific surface area so that the strength of the zeolite adsorbent can be improved. These binders may be used alone or two or more of these in combination.

The carbon compound is a compound that adheres to the zeolite adsorbent along with the use of the zeolite adsorbent (purification of the syngas). In this case, the carbon compound usually adheres to the zeolite material, particularly to a polar surface of the zeolite material. Examples of the carbon compound include, without particular limitation, tar, naphthalene, benzene, ethylbenzene, toluene, 1-naphthol, and the like. The attached amount of the carbon compound is preferably 5.0 mass % or more in terms of carbon atoms, with respect to the zeolite adsorbent. When the attached amount of the carbon compound (in terms of carbon atoms) is 5.0 mass % or more, the adsorption performance of the zeolite to the carbon dioxide may decrease.

The sulfur compound is a compound that adheres to the zeolite adsorbent along with the use of the zeolite adsorbent (purification of the syngas). In this case, the sulfur compound usually adheres to the zeolite material, particularly to a polar surface of the zeolite material. Examples of the sulfur compound include, without particular limitation, hydrogen sulfide, dimethyl sulfide, dimethyl disulfide, thiophene, and the like. The attached amount of the sulfur compound is preferably 0.01 mass % or more in terms of sulfur atoms, with respect to the zeolite adsorbent. When the attached amount of the sulfur compound (in terms of sulfur atoms) is 0.01 mass % or more, the adsorption performance of the zeolite to carbon dioxide may decrease.

The shape of the zeolite adsorbent may be, without particular limitation, in the form of particles or aggregates. In this case, when the zeolite adsorbent is used in the form of an aggregate, the aggregate can be produced by extrusion molding, bead molding, or the like, by using a binder suitable for aggregation, such as clay, silica, alumina, metal oxides, and the like.

The used zeolite adsorbent can be produced by repeating a step of adsorbing a carbon dioxide gas from a syngas containing carbon dioxide to a new (unused) zeolite adsorbent to reduce the carbon dioxide gas concentration in the syngas, and a step of desorbing the adsorbed carbon dioxide from the zeolite adsorbent.

The syngas contains carbon dioxide. In addition, it preferably further includes carbon monoxide, hydrogen, nitrogen, and the like.

Since the used zeolite adsorbent can be deteriorated by the adhesion of the carbon compound and/or the sulfur compound, the syngas may contain the carbon compound and/or the sulfur compound. Adhesion of the carbon compound and/or the sulfur compound may occur simultaneously during adsorption and desorption of the carbon dioxide.

Examples of the carbon compound include, without particular limitation, tar, naphthalene, benzene, ethylbenzene, toluene, 1-naphthol, and the like. These carbon compounds may be contained alone or two or more of these in a mixture.

Examples of the sulfur compound include, without particular limitation, hydrogen sulfide, dimethyl sulfide, dimethyl disulfide, thiophene, and the like. These sulfur compounds may be contained alone or two or more of these in a mixture.

The syngas is preferably derived from plastic waste, raw garbage, municipal waste (MSW), waste tires, biomass waste, household waste, building member waste, coal, petroleum oil, petroleum oil-derived compound, natural gas, and shale gas, more preferably from plastic waste, raw garbage, municipal waste (MSW), waste tires, biomass waste, household waste, and building member waste, further preferably from plastic waste, raw garbage, municipal waste (MSW), waste tires, household waste, more preferably from plastic waste, raw garbage, municipal waste (MSW), waste tires, and household waste, particularly preferably from plastic waste, municipal waste (MSW), and waste tires, and most preferably from municipal waste (MSW). Note that, when the syngas is derived from municipal waste (MSW), biomass waste, household waste, coal, petroleum oil, or petroleum oil-derived compound, the content of the above-described carbon compound and sulfur compound tends to increase when the syngas is prepared, which makes it possible to exert the effect of the present invention even more. This trend may be particularly pronounced for a syngas from municipal waste (MSW). The raw materials of the syngas may be used alone or two or more of those in combination.

The method for adsorbing and desorbing the carbon dioxide gas is, without particular limitation, pressure swing adsorption (PSA), temperature swing adsorption (TSA), pressure temperature swing adsorption (PTSA), and more preferably pressure swing adsorption (PSA). In this case, pressure swing adsorption (PSA), temperature swing adsorption (TSA), and pressure temperature swing adsorption (PTSA) may be combined. In other words, the new (unused) zeolite adsorbent is preferably used in a pressure swing adsorption apparatus, a temperature swing adsorption apparatus, a pressure temperature swing adsorption apparatus, and more preferably in a pressure swing adsorption apparatus. At this time, two or more of the pressure swing adsorption apparatus, temperature swing adsorption apparatus, and pressure temperature swing adsorption apparatus may be used, or they may be used in combination.

In one embodiment, the pressure at the time of adsorption in the case of pressure swing adsorption (PSA) is preferably more than 0 kPa and 100 kPa or less in gauge pressure and more preferably 30 to 70 kPa. On the other hand, the pressure at the time of desorption in the case of pressure swing adsorption (PSA) is preferably −101.3 kPa or more and less than 0 kPa in gauge pressure and more preferably −95 to −80 kPa in gauge pressure.

In one embodiment, the temperature at the time of adsorption in the case of temperature swing adsorption (TSA) is preferably 10 to 50° C. and more preferably 15 to 35° C. On the other hand, the temperature at the time of desorption in the case of temperature swing adsorption (TSA) is preferably 50 to 250° C. and more preferably 100 to 170° C.

Further, in one embodiment, the pressure at the time of adsorption in the case of pressure temperature swing adsorption (PTSA) is preferably more than 0 kPa and 100 kPa or less in gauge pressure and more preferably 30 to 70 kPa in gauge pressure. The temperature at the time of adsorption is preferably 10 to 50° C. and more preferably 15 to 35° C. On the other hand, the pressure at the time of desorption in the case of pressure temperature swing adsorption (PTSA) is preferably −101.3 kPa or more and less than 0 kPa in gauge pressure and more preferably −95 to −80 kPa in gauge pressure. The temperature at the time of desorption is preferably 50 to 200° C. and more preferably −95 to −80 kPa in gauge pressure.

The method for recovering the used zeolite adsorbent is done by, without particular limitation, suspending the adsorption and desorption of carbon dioxide and recovering the used zeolite at that time. Note that it is preferable from the viewpoint of productivity to arrange two or more apparatuses for adsorbing and desorbing carbon dioxide so that while the adsorption and desorption of carbon dioxide is suspended, the other apparatuses for adsorbing and desorbing carbon dioxide is operated.

(Regeneration Step)

A regeneration step is a step of calcining the used zeolite adsorbent at a temperature of 300° C. to 600° C. in an oxygen atmosphere to produce a regenerated zeolite adsorbent (see FIG. 1). In this case, the calcining temperature is preferably 350° C. to 550° C. and more preferably 400° C. to 500° C. When the calcining temperature is 300° C. or higher, the carbon compound attached to the used zeolite adsorbent can be reduced by calcining. On the other hand, when the calcining temperature is 600° C. or less, it is possible to prevent the crystal structure of the zeolite adsorbent from changing or collapsing and to maintain the performance of the regenerated zeolite adsorbent. Therefore, by setting the calcining temperature in the range of 300 to 600° C., the performance of the regenerated zeolite adsorbent can be maintained, and also the carbon compound and the sulfur compound remain in the zeolite adsorbent to an appropriate extent. As a result, the adsorption performance of the regenerated zeolite adsorbent is adjusted, and the absorbent can exhibit a stable purification ability immediately after its start of use. Note that, the attached amount of the carbon compound and/or sulfur compound in the regenerated zeolite adsorbent can be adjusted by appropriate adjustment of the calcination temperature, the calcination time, the calcination pressure, and the like. The degree of regeneration of the zeolite adsorbent can be determined by the degree of temperature escalation of the zeolite adsorbent during calcination (regeneration progresses more as the temperature does not rise), detection of carbon dioxide in the exhaust gas stream (regeneration progresses more as the carbon dioxide concentration in the exhaust gas stream is not detected), and the like.

The calcination in the regeneration step is usually carried out under an oxygen atmosphere. In this case, it is preferable that oxygen (or air) is gradually introduced to gradually increase the oxygen concentration in order to avoid an excessive temperature escalation due to calcination of carbon. The final oxygen concentration of calcination in the regeneration step may be high; however, in view of economic efficiency, it is 30% or less and preferably 0.1 to 21%. Air can be used up until the concentration is 21%, which is more economically efficient. Preferred example as the component other than oxygen is an inert gas such as nitrogen, helium, or argon. In particular, when air is used as the oxygen-containing gas, it is preferable to use dry air or air which has been subjected to a dehydration treatment.

The calcination time is, without particular limitation, preferably 24 hours or less, more preferably 1 to 12 hours, and particularly preferably 2 to 6 hours, from the viewpoint of energy used for calcination. Preferably, the calcination time is 24 hours or less since thermal history can be suppressed and cycle life of repetition can be prolonged.

The attached amount of the carbon compound of the regenerated zeolite adsorbent is preferably 1.0 mass % or less, more preferably 0.02 mass % to 0.80 mass %, further preferably 0.04 mass % to 0.70 mass %, particularly preferably 0.06 mass % to 0.70 mass %, and most preferably 0.08 mass % to 0.20 mass % in terms of carbon atoms with respect to the zeolite adsorbent. When the attached amount of the carbon compound (in terms of carbon atoms) is 1.00 mass % or less, the performance of the regenerated zeolite adsorbent is close to the performance of the new zeolite adsorbent in a state after being stabilized from the start of use, and it is preferable since the zeolite adsorbent can be used for a period substantially similar to that of the new zeolite. The attached amount of the carbon compound (in terms of carbon atoms) is preferably 0.02 mass % or more since it is possible to prevent unstable purification due to excessive purification ability of the zeolite immediately after the start of use.

The attached amount of the sulfur compound of the regenerated zeolite adsorbent is preferably 0.01 mass % to 0.8 mass %, more preferably 0.01 mass % to 0.8 mass %, further preferably 0.02 mass % to 0.6 mass %, and particularly preferably 0.03 mass % to 0.4 mass %, in terms of sulfur atoms with respect to the zeolite adsorbent. It is preferable that the attached amount of the sulfur compound in the calcined zeolite adsorbent (in terms of sulfur atoms) is 0.01 mass % or more, because the adsorption performance can be stabilized immediately after the start of use. On the other hand, when the attached amount of the sulfur compound (in terms of sulfur atoms) is 0.8 mass % or less, it is possible to prevent the adsorption performance from being affected adversely.

(Reuse Step)

A reuse step is a step of reusing the regenerated zeolite adsorbent (see FIG. 1). Since the adsorption performance of the regenerated zeolite adsorbent is controlled as described above, it is possible to stably exhibit the same adsorption performance as that of before replacement from immediately after the start of use. Therefore, the composition of the syngas purified in the syngas purification step described below has been appropriately adjusted, and microbial fermentation of the syngas can be efficiently performed in the subsequent microbial fermentation step.

<Regenerated Adsorbent>

A regenerated adsorbent is a zeolite adsorbent obtained by regenerating the used zeolite adsorbent. In this case, the carbon compound and the sulfur compound are attached to the regenerated zeolite adsorbent, and the attached amount of the carbon compound is 1.0 mass % or less in terms of carbon atoms with respect to the zeolite adsorbent, and the attached amount of the sulfur compound is 0.01 mass % to 0.8 mass % in terms of sulfur atoms with respect to the zeolite adsorbent.

Preferred attached amounts of the carbon compound and the sulfur compound of the regenerated zeolite adsorbent are as described above.

The structure of the zeolite adsorbent, specifically, the zeolite, binder, etc. contained in the zeolite adsorbent, and the shape of the zeolite adsorbent, etc., are preferably equivalent to those of the used zeolite adsorbent, and are more preferably the same. In this case, said "equivalent" means when the regenerated zeolite adsorbent is used to produce a reused adsorbent in which the absorption amount of the carbon compound and the absorption amount of the sulfur compound are the same as those of the said used adsorbent, and when the reused adsorbent is subsequently measured for its absorption amount of the carbon dioxide, the absorption ability of carbon dioxide of the used absorbent and the absorption ability of carbon dioxide of the reused absorbent is within the range of 10%. Further, said "same" means that the absorption ability of carbon dioxide of the used absorbent and the absorption ability of carbon dioxide of the reused absorbent is the same.

The regenerated adsorbent can be produced, for example, by the above-described method for reusing a zeolite adsorbent.

<Method for Manufacturing Organic Substance>

A method for manufacturing an organic substance is a method in which an organic substance is manufactured by microbial fermentation from a purified syngas using the regenerated zeolite adsorbent. The manufacturing method comprises a syngas purification step and a microbial fermentation step. Hereinafter, one example of the method for manufacturing an organic substance according to the present invention will be described in details.

Figure 2:
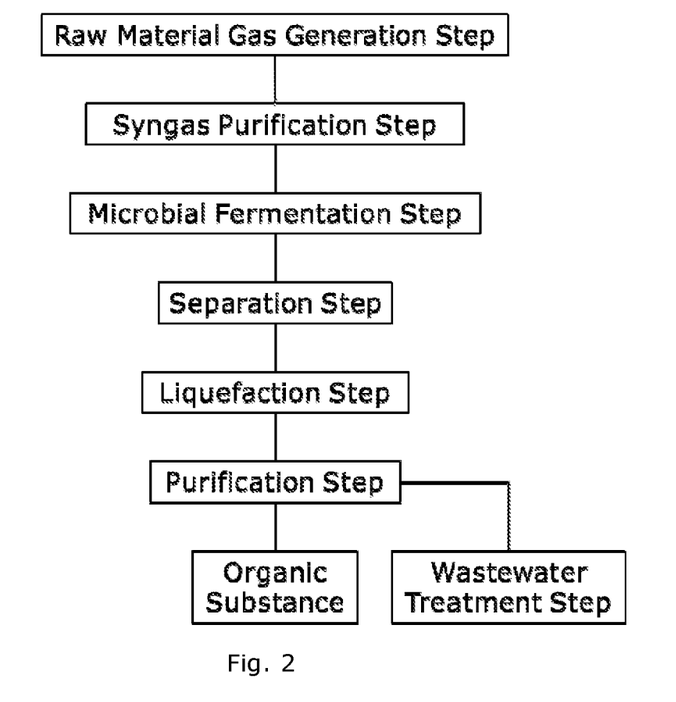
FIG. 2 is a process flow diagram showing one example of a method for producing an organic substance according to the present invention.

First, one example of the method for manufacturing an organic substance according to the present invention will be described with reference to the drawings. FIG. 2 is a process flow diagram showing one example of the method for manufacturing an organic substance. The method for manufacturing an organic substance shown in FIG. 2 comprises a microbial fermentation step of supplying a syngas containing carbon monoxide to a microbial fermentation tank to obtain an organic substance-containing liquid by microbial fermentation, a separation step of separating the organic substance-containing liquid into a liquid or solid component comprising the microorganisms and a gaseous component comprising the organic substance, a liquefaction step of condensing and liquefying the gaseous component, and a purification step of purifying the organic substance from the liquid product obtained in the liquefaction step. In addition, there may be included a raw material gas generation step, a syngas preparation step, a waste water treatment step, and the like if necessary. Each step will be described below.

<Raw Material Gas Generation Step>

A raw material gas generation step is a step of generating a raw material gas by gasifying a carbon source in a gasification portion (see FIG. 2). A gasification furnace may be used in the raw material gas generation step. The gasification furnace is a furnace for burning a carbon source (incomplete combustion), and examples thereof include a shaft furnace, a kiln furnace, a fluidized bed furnace, a gasification reforming furnace, and the like. The gasification furnace is preferably a fluidized bed furnace type since it is possible to achieve a high load of the hearth and excellent operability by partial combustion of waste. The waste is gasified in the fluidized bed furnace at a low temperature (about 450 to 600° C.) and in a low oxygen atmosphere to decompose into gas (carbon monoxide, carbon dioxide, hydrogen, methane, etc.) and char containing a large amount of carbon. In addition, since incombustibles contained in the waste are separated from the bottom of the furnace in a sanitary and low-oxidation state, valuable materials such as iron and aluminum in the incombustibles can be selectively recovered. Therefore, gasification of such waste enables efficient resource recycling.

The gasification temperature in the raw material gas generation step is usually 100° C. to 1500° C. and preferably 200° C. to 1200° C.

The reaction time of gasification in the raw material gas generation step is usually 2 seconds or more and preferably 5 seconds or more.

The carbon source used in the raw material gas generation step is, without particular limitation, coal used in a coke oven, blast furnace (blast furnace gas), converter of a steel plant or a coal-fired power plant; general waste introduced into an incinerator (especially gasification furnace) and industrial waste; and various carbon-containing materials for the purpose of recycling carbon dioxide, etc. which is subgenerated in various industries.

Specifically, examples of the carbon source include plastic waste, garbage, municipal waste (MSW), waste tyres, biomass waste, household waste such as duvets and papers, waste such as building members, coal, petroleum oil, compounds derived from petroleum oil, natural gas, shale gas, and the like, and preferred amongst these is various waste, and more preferably non-segregated municipal waste from the view point of segregation costs.

The raw material gas obtained by gasifying the carbon source includes carbon dioxide, carbon monoxide, and hydrogen, but may further include oxygen and nitrogen. As other components, the raw material gas may further include components such as a carbon compound, a sulfur compound, soot, a nitrogen compound, a phosphorus compound, and an aromatic compound.

The raw material gas may be produced as a gas containing preferably 0.1 vol % or more, more preferably 10 vol % or more, and further preferably 20 vol % or more of carbon monoxide by performing heat treatment (commonly known as gasification) for carrying out combustion (incomplete combustion) of the carbon source in the raw material gas generation step, that is, by partially oxidizing the carbon source.

<Syngas Purification Step>

A syngas purification step is a step of removing or reducing specific substances such as various contaminants, dust particles, impurities, and undesirable amounts of compounds from the raw material gas (see FIG. 2). When the raw material gas is derived from waste, it usually tends to contain 0.1 to 80 vol % of carbon monoxide, 0.1 to 40 vol % of carbon dioxide, 0.1 to 80 vol % of hydrogen, and further 1 ppm or more of a nitrogen compound, 1 ppm or more of a sulfur compound, 0.1 ppm or more of a phosphorus compound, and/or 10 ppm or more of an aromatic compound. It may also contain other substances such as environmental pollutants, dust particles, and impurities. For this reason, when the syngas is supplied to the microbial fermentation tank, it is preferable to reduce or remove from the raw material gas, substances that are not favorable for stable culture of microorganisms and compounds in an undesirable amount, so that the content of each component contained in the raw material gas is within a range suitable for the stable culture of microorganisms.

Particularly, the concentration of carbon dioxide gas in the syngas is reduced by using the above-described regenerated zeolite adsorbent in the syngas purification step. In this case, the regenerated zeolite adsorbent is used in a pressure swing adsorption apparatus, a temperature swing adsorption apparatus, a pressure temperature swing adsorption apparatus (PTSA), and the like.

Further, the syngas may be subjected to other treatment steps known in the art to remove the impurities and adjust the gas composition. As for the other treatment steps, for example, treatment can be done using one or two or more of a gas chiller (moisture separator), a low-temperature separation system (deep-cooling system) separator, a cyclone, a fine particle (soot) separator such as a bag filter, a scrubber (water-soluble impurity separator), a desulfurization unit (sulfide separator), a membrane separation system separator, a deoxidation apparatus, a separator using activated carbon, a separator using a copper catalyst or a palladium catalyst, and the like. Additionally, treatment can be done using one or two more of a pressure swing adsorption apparatus (PSA) using an adsorbent other than the regenerated zeolite material, a temperature swing adsorption apparatus (TSA), and a pressure-temperature swing adsorption type separation apparatus (PTSA).

The syngas used in the method for producing an organic substance contains at least carbon monoxide as an essential component, and may further contain hydrogen, carbon dioxide, and nitrogen.

The syngas used in the present invention may be a gas obtained by generating a raw material gas by gasifying a carbon source (raw material gas generation step) and then along with adjusting the concentration of each component of carbon monoxide, carbon dioxide, hydrogen and nitrogen, reducing or removing the above-mentioned substances or compounds from the raw material gas.

The concentration of carbon monoxide in the syngas is usually 20 vol % to 80 vol %, preferably 25 vol % to 50 vol %, and more preferably 35 vol % to 45 vol %, with respect to the total concentration of carbon monoxide, carbon dioxide, hydrogen, and nitrogen in the syngas.

The concentration of hydrogen in the syngas is usually 10 vol % to 80 vol %, preferably 30 vol % to 55 vol %, and more preferably 40 vol % to 50 vol %, with respect to the total concentration of carbon monoxide, carbon dioxide, hydrogen and nitrogen in the syngas.

The concentration of carbon dioxide in the syngas is usually 0.1 vol % to 40 vol %, preferably 0.3 vol % to 30 vol %, more preferably 0.5 vol % to 10 vol %, and particularly preferably 1 vol % to 6 vol %, with respect to the total concentration of carbon monoxide, carbon dioxide, hydrogen and nitrogen in the syngas.

The concentration of nitrogen in the syngas is usually 40 vol % or less, preferably 1 vol % to 20 vol %, and more preferably 5 vol % to 15 vol %, with respect to the total concentration of carbon monoxide, carbon dioxide, hydrogen and nitrogen in the syngas.

The concentrations of carbon monoxide, carbon dioxide, hydrogen and nitrogen can be set to a predetermined range by changing the C—H—N element composition of the carbon source in the raw material gas generation step or by appropriately changing the combustion conditions such as the combustion temperature and the oxygen concentration of the gas supplied during combustion. For example, when the concentration of carbon monoxide or hydrogen is to be changed, the carbon source is changed to a carbon source having a high C—H ratio such as waste plastic, and when the nitrogen concentration is to be decreased, gas having a high oxygen concentration is supplied in the raw material gas generation process.

The syngas used in the present invention is not particularly limited to the above components, and may contain a sulfur compound, a phosphorus compound, a nitrogen compound, and the like. The content of each of these compounds is preferably 0.05 ppm or more, more preferably 0.1 ppm or more, further preferably 0.5 ppm or more, and preferably 2000 ppm or less, more preferably 1000 ppm or less, further preferably 80 ppm or less, further more preferably 60 ppm or less, and particularly preferably 40 ppm or less.

<Microbial Fermentation Step>

A microbial fermentation step is a step of producing an organic substance by microbial fermentation of the above syngas in a microbial fermentation tank (see FIG. 2). The microbial fermentation tank is preferably a continuous fermentation apparatus. Generally, the microbial fermentation tank can be of any shape, and examples thereof include a stirring type, an air lift type, a bubble column type, a loop type, an open bond type, and a photo-bio type; however, in the present invention, suitable use can be made to a known loop reactor in which the microbial fermentation tank has a main tank portion and a reflux portion. In this case, it is preferable to further comprise a circulation step of circulating the liquid medium between the main tank portion and the reflux portion.

As for the syngas to be supplied to the microbial fermentation tank, the gas obtained through the raw material gas generation step may be used as the syngas as it is as long as the above-described component conditions of the syngas are satisfied, or the syngas may be used after adding another predetermined gas to the gas from which impurities or the like have been reduced or removed from the raw material gas. As another predetermined gas, at least one compound selected from the group consisting of a sulfur compound such as sulfur dioxide, a phosphorus compound, and a nitrogen compound may be added to form the syngas.

The syngas and the microbial culture solution may be continuously supplied to the microbial fermentation tank; there is no need to supply the syngas and the microbial culture solution simultaneously, and the syngas may be supplied to the microbial fermentation tank to which the microbial culture solution has been supplied in advance. It is known that certain kinds of anaerobic microorganisms produce valuable organic substances such as ethanol from a substrate gas such as syngas by fermentation action, and these kinds of gas-utilizing microorganisms are cultured in a liquid medium. For example, the liquid medium and the gas-utilizing bacteria may be supplied and accommodated, and while stirring the liquid medium in this state, the syngas may be supplied into the microbial fermentation tank. Thus, the gas-utilizing bacteria are cultured in a liquid medium, and its fermentation action makes it possible to produce an organic substance from the syngas.

In the microbial fermentation tank, the temperature of the culture medium, etc. (culture temperature) may be any temperature, and is preferably about 30 to 45° C., more preferably about 33 to 42° C., and further preferably about 36.5 to 37.5° C. The culture time is preferably 12 hours or more, more preferably 7 days or more, particularly preferably 30 days or more, and most preferably 60 days or more in continuous culture, with no particular limitation set to the upper limit; however from the viewpoint of regular maintenance of the facilities, the time is preferably 720 days or less and more preferably 365 days or less. The term culture time means the time from the time when the seed bacteria are added to the culture tank to the time when the whole amount of the culture solution in the culture tank is discharged.

The microorganism (species) contained in the microorganism culture solution is not particularly limited as long as the desired organic substance can be produced by microbial fermentation of the syngas using carbon monoxide as a main raw material (see FIG. 2). For example, the microorganisms (species) are preferably microorganisms that generate an organic substance from the syngas by the fermentation action of gas-utilizing bacteria, particularly preferably microorganisms having a metabolic pathway of acetyl COA. Among the gas-utilizing bacteria, the genus *Clostridium* is more preferred, and *Clostridium autoethanogenum* is particularly preferred, with no particular limitation thereto. The following is a further example.

Gas-utilizing bacteria include both eubacteria and archaebacteria. Examples of the eubacteria include *Clostridium, Moorella, Acetobacterium, Carboxydocella, Rhodopseudomonas, Eubacterium, Butyribacterium, Oligotropha, Bradyrhizobium*, and Ralsotonia bacteria which are aerobic hydrogen-oxidizing bacteria, and the like.

On the other hand, examples of the archaebacteria include *Methanobacterium* sp., *Methanobrevibacter* sp., *Methanocalculus* sp., *Methanococcus* sp., *Methanosarcina* sp., *Methanosphaera* sp., *Methanothermobacter* sp., *Methanothrix* sp., *Methanoculleus* sp., *Methanofollis* sp., *Methanogenium* sp., *Methanospirillium* sp., *Methanosaeta* sp., *Thermococcus* sp., *Thermofilum* sp., and *Arcaheoglobus* sp. Among these, preferred archaebacteria are *Methanosarcina* sp., *Methanococcus* sp., *Methanothermobacter* sp., *Methanothrix* sp., *Thermococcus* sp., *Thermofilum* sp. and *Archaeoglobus* sp.

Further, *Methanosarcina* sp., *Methanothermobactor* sp. or *Methanococcus* sp. is preferred as the archaebacteria since they have excellent carbon monoxide and carbon dioxide utilizing properties, and *Methanosarcina* sp. or *Methanococcus* sp. is particularly preferred. Specific examples of the genus *Methanosarcina* include *Methanosarcina barkeri, Methanosarcina mazei*, and *Methanosarcina acetivorans*.

Among the above-described gas-utilizing bacteria, bacteria having a high ability to produce the desired organic substance is selected and used. Examples of the gas-utilizing bacterium having a high ability to produce ethanol, for example include *Clostridium autoethanogenum, Clostridium ljungdahlii, Clostridium aceticum, Clostridium carboxidivorans, Moorella thermoacetica*, and *Acetobacterium woodii*, among which *Clostridium autoethanogenum* is particularly preferred.

The culture medium used for culturing the above-described microorganism (species) is not particularly limited, as long as it has an appropriate composition according to the fungi, and it is a liquid containing water as a main component and nutrients (for example, vitamins, phosphoric acid, etc.) dissolved or dispersed in the water. The composition of such a culture medium is adjusted so that the gas-utilizing bacteria can grow well. For example, the culture medium in the case where the genus *Clostridium* is used as the microorganism can be obtained by referring to "0097" to "0099" of US Patent Application Publication No. 2017/260552.

The organic substance-containing liquid obtained by the microbial fermentation step can be obtained as a suspension containing microorganisms, dead microorganisms, proteins derived from microorganisms, and the like. Although the protein concentration in the suspension depends on the kind of microorganism, it is usually between 30 and 1000 mg/L. The protein concentration in the organic substance-containing liquid can be measured by the Kjeldahl method.

<Separation Step>

The organic substance-containing liquid obtained by the microbial fermentation step is then subjected to a separation step. In the present invention, the organic substance-containing liquid is heated to room temperature to 500° C. under the condition of 0.01 to 1000 kPa (absolute pressure) to separate into a liquid or solid component comprising the microorganisms and a gaseous component comprising the organic substance (see FIG. 2).

In the conventional method, the organic substance-containing liquid obtained by a microbial fermentation step was distilled so that the desired organic substance was separated and purified; however continuous operation was sometimes hindered because when the organic substance-containing liquid was distilled as it is, foaming occurs in the distillation apparatus since the organic substance-containing liquid contained the microorganisms, proteins derived from the microorganisms, and the like. Further, although it is known that a membrane evaporator is used as a method for purifying a foaming liquid, the membrane evaporator is not suitable for purifying a liquid containing a solid component as its concentration efficiency is low. The present invention is an invention in which the organic substance-containing liquid is heated to separate the liquid or solid component containing the microorganisms and the gaseous component containing the organic substance before separating and purifying the desired organic substance from the organic substance-containing liquid obtained in the microbial fermentation step by distillation operation, etc., and the desired organic substance is separated and purified only from the separated gaseous component containing the organic substance. Carrying out the separation step will prevent the foaming from occurring in the distillation apparatus, so that continuous distillation operation can be carried out in the distillation operation when the organic substance is separated and purified. Further, since the concentration of the organic substance contained in the gaseous component containing the organic substance becomes higher than the concentration of the organic substance contained in the organic substance-containing liquid, the organic substance can be efficiently separated and purified in the purification step which is to be described later.

In the present invention, from the viewpoint of efficiently separating the liquid or solid component comprising the microorganisms, dead microorganisms, proteins derived from the microorganisms, and the like, and the gaseous component comprising the organic substance, the organic substance-containing liquid is heated preferably under a condition of 10 to 200 kPa in absolute pressure, more preferably under a condition of 50 to 150 kPa, and further preferably under normal pressure, and at a temperature of 50 to 200° C., more preferably at a temperature of 80 to 180° C., and further preferably at a temperature of 100 to 150° C.

The heating time in the separation step is not particularly limited as long as a gaseous component can be obtained, and it is usually 5 seconds to 2 hours, preferably 5 seconds to 1 hour, and more preferably 5 seconds to 30 minutes, from the viewpoint of efficiency or economic efficiency.

Any kind of apparatuses may be used in the above-described separation step without particular limitation, as long as the apparatus can efficiently separate the organic substance-containing liquid into a liquid or solid component (microorganisms, dead microorganisms, proteins derived from the microorganisms, etc.) and a gaseous component (the organic substance) by heat energy, and for example, a drying apparatus such as a rotary dryer, a fluidized bed dryer, a vacuum type dryer, or a conduction heating type dryer can be used, and preferably used is a conduction heating type dryer from the viewpoint of efficiency in separating the organic substance-containing liquid having a low solid component concentration into a liquid or solid component and a gaseous component. Examples of the conduction heating type dryer include a drum type dryer and a disk type dryer.

<Liquefaction Step>

A liquefaction step is a step of liquefying the gaseous component containing the organic substance obtained in the separation step by condensation (see FIG. 2). The apparatus used in the liquefaction step is not particularly limited, and preferably used is a heat exchanger, particularly a condenser. Examples of the condenser include a water-cooled condenser, an air-cooled condenser, and an evaporation condenser, among which the water-cooled condenser is preferred. The condenser may be of a single stage or a plurality of stages.

It can be said that the liquefied product obtained by the liquefaction step preferably does not contain components contained in the organic substance-containing liquid such as the microorganisms, dead microorganisms, proteins derived from the microorganisms, and the like; however, the present invention does not exclude the presence of proteins in the liquefied product. Even when proteins are contained in the liquefied product, the concentration thereof is preferably 40 mg/L or less, more preferably 20 mg/L or less, and further preferably 15 mg/L or less.

The condensation heat of the gaseous component obtained by the condenser may be reused as a heat source in the purification step to be described later. By reusing the condensation heat, an organic substance can be produced efficiently and economically efficiently.

<Purification Step>

Next, the organic substance is purified from the liquefied product obtained in the liquefaction step (see FIG. 2). The organic substance-containing liquid obtained in the microorganism fermentation step can be supplied to the purification step without having to undergo the above-described separation step when components such as microorganisms have already been removed. A purification step is a step of separating the organic substance-containing liquid obtained in the liquefaction step into a distillate with increased concentration of the target organic substance and a can distillate obtained by decreasing the concentration of the target organic substance (see FIG. 2). Examples of the apparatus used in the purification step include a distillation apparatus, a treatment apparatus including a pervaporation membrane, a treatment apparatus including a zeolite dehydration membrane, a treatment apparatus for removing a low boiling point substance having a boiling point lower than that of the organic substance, a treatment apparatus for removing a high boiling point substance having a boiling point higher than that of the organic substance, and a treatment apparatus including an ion exchange membrane. These apparatuses may be used alone or in combination of two or more. As the unit operation, heat distillation or membrane separation may be suitably used.

By employing a distillation apparatus in the heat distillation, the desired organic substance can be obtained in a high purity as a distillate. The temperature in the distillation vessel during the distillation of the organic substance (particularly ethanol) is not particularly limited, and is preferably 100° C. or less and more preferably about 70 to 95° C. By setting the temperature in the distillation vessel within the above range, it is possible to ensure separation of the necessary organic substance from the other components, that is, distillation of the organic substance can be ensured more.

The pressure in the distillation apparatus during the distillation of the organic substance may be at a normal pressure, or is preferably less than atmospheric pressure and more preferably about 60 to 95 kPa (absolute pressure). By setting the pressure in the distillation apparatus within the above range, the separation efficiency of the organic substance can be improved, and consequently the yield of the organic substance can be improved. Although depending on the type of the desired organic substance, for example, the yield when the obtained organic substance is ethanol (concentration of ethanol contained in the distillate after distillation) is preferably 90 mass % or more and more preferably 95 mass % or more.

In the membrane separation, a well-known separation membrane can be suitably used, and for example, a zeolite membrane can be suitably used.

The concentration of the organic substance contained in the distillate which was separated in the purification step is preferably 20 mass % to 99.99 mass % and more preferably 60 mass % to 99.9 mass %. On the other hand, the concentration of the organic substance contained in the can liquid is preferably 0.001 mass % to 10 mass % and more preferably 0.01 mass % to 5 mass %.

The can liquid separated in the purification step is substantially free of a nitrogen compound. In the present invention, "substantially free" does not mean that the concentration of the nitrogen compound is 0 ppm, but means that the concentration of the nitrogen compound in the can liquid obtained in the purification step is such that the waste water treatment step is unnecessary. In the separation step, the desired organic substance is not purified from the organic substance-containing liquid obtained in the microbial fermentation step, but the organic substance-containing liquid is separated into the liquid or solid component containing the microorganisms and the gaseous component containing the organic substance as described above. In this case, the gaseous component containing the organic substance contains almost no nitrogen compound since the nitrogen compound remains on the liquid or solid component side containing the microorganisms. Therefore, it is considered that the can liquid obtained when the organic substance is purified from the liquefied product obtained by liquefying the gaseous component is substantially free of the nitrogen compound. Even when the can liquid contains a nitrogen compound, the concentration of the nitrogen compound is 0.1 to 200 ppm, preferably 0.1 to 100 ppm, and more preferably 0.1 to 50 ppm.

For the same reason as described above, the can liquid separated in the purification step is substantially free of a phosphorus compound. It should be noted that "substantially free" does not mean that the concentration of the phosphorus compound is 0 ppm, but means that the concentration of the phosphorus compound in the can liquid obtained in the purification step is such that the waste water treatment step is unnecessary. Even when the can liquid contains a phosphorus compound, the concentration of the phosphorus compound is 0.1 to 100 ppm, preferably 0.1 to 50 ppm, and more preferably 0.1 to 25 ppm. As described above, according to the method of the present invention, it is considered that the can liquid discharged in the purification step of the organic substance is substantially free of the nitrogen compound or the phosphorus compound, or hardly contains other organic substances, so that the waste water treatment process can be simplified which was conventionally required.

<Wastewater Treatment Process>

The can liquid separated in the purification step may be supplied to the waste water treatment step (see FIG. 2). In the waste water treatment step, organic substances such as nitrogen compounds and phosphorus compounds can be further removed from the can liquid. In this step, the organic substance may be removed by anaerobic treatment or aerobic treatment of the can liquid. The removed organic substance may be used as a fuel (heat source) in the purification step.

The treatment temperature in the waste water treatment step is usually 0 to 90° C., preferably 20 to 40° C., and more preferably 30 to 40° C.

Since the liquid or solid component comprising the microorganisms and the like are removed from the can liquid obtained through the separation step, load like the waste water treatment and the like is reduced compared with the can liquid obtained by being directly supplied to the purification step from the microbial fermentation step.

In the waste water treatment step, the concentration of the nitrogen compound in the treated liquid obtained by treating the can liquid is preferably 0.1 to 30 ppm, more preferably 0.1 to 20 ppm, further preferably 0.1 to 10 ppm, and particularly preferably, the nitrogen compound is not contained. The concentration of the phosphorus compound in the treated liquid is preferably 0.1 to 10 ppm, more preferably 0.1 to 5 ppm, further preferably 0.1 to 1 ppm, and particularly preferably, no phosphorus compound contained in the can liquid.

<Organic Substance and Use Thereof>

Examples of the organic substance obtained by the production method according to the present invention include methanol, ethanol, 2,3-butanediol, acetic acid, lactic acid, isoprene, butadiene and the like, preferably containing alcohols or diols having 1 to 6 carbons, more preferably containing alcohols or diols having 1 to 4 carbons, and further preferably ethanol. The use of the organic substance obtained by the production method of the present invention is not particularly limited. The produced organic substance can be used, for example, as a raw material for plastics, resins and the like, or as various solvents, disinfectants or fuels. High-concentration ethanol can be used as fuel ethanol mixed with gasoline or the like, and can also be used as additives in cosmetics, beverages, chemical substances, raw materials such as fuel (jet fuel), food and the like, and has extremely high versatility.

EXAMPLES

The present invention will be described in more details with reference to Examples; however, the present invention is not limited to the following Examples to the extent the key of the invention is not exceeded.

Example 1

A new (unused) zeolite adsorbent containing LSX zeolite adsorbent as the main component was inserted into a pressure swing absorption apparatus. The attached amount of the carbon compound in the zeolite adsorbent was 0.09 mass % in terms of carbon atoms with respect to the zeolite adsorbent, and the attached amount of the sulfur compound in the zeolite adsorbent was 0.002 mass % in terms of sulfur atoms with respect to the zeolite adsorbent. The attached amount of the carbon compound in the zeolite adsorbent (in terms of carbon atoms) was measured by an NC corder method using a total nitrogen/total carbon measuring apparatus SUMIGRAPH NC-22F (manufactured by Sumitomo Chemical Analysis Center). The attached amount of the sulfur compound (in terms of sulfur atoms) was measured using an ion chromatograph (anion analysis system) ICS1500 (manufactured by DIONEX) after the sample was calcined in a combustion tube of an analyzer using an automatic sample combustion apparatus AQF-100 (manufactured by Mitsubishi Chemical Corporation) and absorbing the generated gas into the absorbing liquid. The details are as follows.

Measurement of carbon atom adsorption amount (mass %): NC corder method
<Instrument Used>
Instrument: NC-22F (manufactured by Sumitomo Chemical Analysis Center)
Reduction furnace: 600° C.
Helium gas: 80 mL/min Oxygen gas: 350 mL/min
Detector: TCD (Thermal Conductivity Detector)
Pre-treatment: adsorbent measured was one which was lyophilized and crushed beforehand
Measurement of Sulfur Atom Adsorption Amount (μg/g)
<Combustion and Absorption Conditions>
System: AQF-100 (manufactured by Mitsubishi Chemical Corporation)
Electric furnace temperature: Inlet 1000° C. Outlet 1100° C.
Gases: Ar/$O_2$ 200 mL/min
$O_2$ 400 mL/min
Absorbing liquid: $H_2O_2$ 0.036%), internal standard Br 2 μg/mL
Absorbing liquid volume: 10 mL
<Ion Chromatography/Anion Analysis Conditions>
System: ICS1500 (manufactured by DIONEX)
Mobile phase: 2.7 mmol/L $Na_2CO_3$/0.3 mmol/L $NaHCO_3$
Flow rate: 1.50 mL/min.
Detector: electrical conductivity detector
Injection volume: 100 μL Next, syngas containing hydrogen gas, nitrogen gas, carbon monoxide gas, and carbon dioxide gas as main components, which was discharged from the gasification furnace, was prepared, and the syngas was supplied to a pressure swing adsorption apparatus, and the carbon dioxide gas in the syngas was adsorbed on a zeolite adsorbent to purify the syngas. The syngas was purified over a long period of time (the number of times of adsorption and desorption: about 50,000 times), and the supply of the syngas was stopped when the attached amount of the carbon compound of the zeolite adsorbent in the pressure swing adsorption apparatus became 5.7 mass % in terms of carbon atoms, with respect to the zeolite adsorbent.

Subsequently, when the used zeolite adsorbent was recovered from the pressure swing adsorption apparatus, the attached amount of the carbon compound of the zeolite adsorbent was 5.7 mass % in terms of carbon atoms, with respect to the zeolite absorbent, and the attached amount of the sulfur compound was 0.22 mass % in terms of sulfur atoms, with respect to the zeolite absorbent.

Next, the recovered zeolite adsorbent was calcined at a temperature of 400° C. under an oxygen atmosphere. After carbon dioxide was no longer detected in the exhaust gas stream, calcination was stopped, and a regenerated zeolite adsorbent was obtained. The attached amount of the carbon compound of the regenerated zeolite adsorbent was 0.19 mass % in terms of carbon atoms, with respect to the zeolite adsorbent, and the attached amount of the sulfur compound was 0.23 mass % in terms of sulfur atoms, with respect to the zeolite adsorbent. As a result of calcining at a relatively low temperature of 400° C., 96.7% of the carbon compound attaching to the zeolite adsorbent was removed. The sulfur compound remained. As a result, it can be said that the carbon compound and the sulfur compound moderately remain in the obtained regenerated zeolite adsorbent.

Next, when the regenerated zeolite adsorbent was filled in the pressure swing adsorption apparatus and used again as the adsorbent, the adsorption performance was stably exhibited, and the composition of the syngas purified about 2.5 hours after the start of the operation of the pressure swing adsorption apparatus was stable.

Thereafter, the purified syngas was supplied to the microbial fermentation tank, and the organic substance was finally obtained efficiently through undergoing the microbial fermentation step, separation step, liquefaction step, and purification step.

Comparative Example 1

When a new (unused) zeolite adsorbent was filled in the pressure swing adsorption apparatus instead of the regenerated zeolite adsorbent after recovering the used zeolite adsorbent from the pressure swing adsorption apparatus, the adsorption performance was unstable for about 7 hours after the start of the operation of the pressure swing adsorption apparatus, and the composition of the purified syngas was unstable. As such, although the purified syngas was supplied to the microbial fermentation tank, the efficiency of microbial fermentation decreased and the yield of the final organic substance also decreased.

The invention claimed is:

1. A method for regenerating a zeolite adsorbent which adsorbs a carbon dioxide gas from a syngas comprising the carbon dioxide gas and reduces the concentration of the carbon dioxide gas in the syngas, comprising:
   a step of recovering a used zeolite adsorbent;
   a step of calcining the used zeolite adsorbent at a temperature of 300° C. to 600° C. in an oxygen atmosphere to produce a regenerated zeolite adsorbent; and
   a step of reusing the regenerated zeolite adsorbent;
   wherein the zeolite adsorbent comprises an LSX type zeolite.

2. The method according to claim 1, wherein
   the step of recovering the used zeolite adsorbent comprises recovering the used zeolite adsorbent from a pressure swing adsorption apparatus.

3. The method according to claim 1, wherein
   the method is a method for regenerating a zeolite adsorbent which adsorbs a carbon dioxide gas from a syngas comprising the carbon dioxide gas and a tar component and reduces the concentration of the carbon dioxide gas in the syngas.

4. The method according to claim 1, wherein
   the method is a method for regenerating a zeolite adsorbent which adsorbs a carbon dioxide gas from a syngas comprising the carbon dioxide gas, carbon monoxide, hydrogen, and nitrogen and reduces the concentration of the carbon dioxide gas in the syngas.

5. The method according to claim 1, wherein
   the method is a method for regenerating a zeolite adsorbent which (i) adsorbs a carbon dioxide gas from a syngas which comprises the carbon dioxide gas and which is derived from municipal waste and (ii) reduces the concentration of the carbon dioxide gas in the syngas.

6. A regenerated zeolite adsorbent obtained by regenerating a used zeolite adsorbent, wherein
   a carbon compound and a sulfur compound are attached to the regenerated zeolite adsorbent, and wherein
   the attached amount of the carbon compound is 1.0 mass % or less in terms of carbon atoms, with respect to the zeolite adsorbent, and
   the attached amount of the sulfur compound is 0.01 to 0.8 mass % in terms of sulfur atoms, with respect to the zeolite adsorbent, wherein the zeolite adsorbent comprises an LSX type zeolite.

\* \* \* \* \*